US00PP10658P

United States Patent [19]

Mukundan et al.

[11] Patent Number: Plant 10,658

[45] Date of Patent: Oct. 20, 1998

[54] AGLAONEMA PLANT NAMED 'JEWEL OF INDIA'

[76] Inventors: Parthasarathy Mukundan; Gopalaswamy Parthasarathy, both of "Srinivasa" 237/46 Fifth Main Road, Chamarajpet, Bangalore, India

[21] Appl. No.: 920,468

[22] Filed: Aug. 29, 1997

[51] Int. Cl.[6] ..... A01H 5/00

[52] U.S. Cl. ..... Plt./88.1

[58] Field of Search ..... Plt./88.1

*Primary Examiner*—Howard J. Locker
*Assistant Examiner*—Kent L. Bell
*Attorney, Agent, or Firm*—C. A. Whealy

[57] ABSTRACT

A new and distinct cultivar of Aglaonema named 'Jewel of India' particularly characterized by its rapid growth rate; compact growth habit; unique and distinct multicolored foliage pattern with prominent and persistent dark green and grayed green spots and blotches on shiny silvery green leaves; dark green leaf margin; narrowly lanceolate and relatively small leaves; marbled leaf petioles; numerous divisions; full and dense appearance; rapid rooting; good postproduction longevity; tolerance of low winter temperatures; and exceptional resistance to diseases common to Aglaonema.

2 Drawing Sheets

The present invention relates to a new and distinct cultivar of Aglaonema plant, botanically known as *Aglaonema hybrida,* evaluated under the code name AG-6, and hereinafter referred to by the cultivar name 'Jewel of India'.

The new cultivar is a product of a planned breeding program conducted by the inventors in Bangalore, India. The objective of the breeding program was to create new Aglaonema cultivars having unique foliage color patterns, desirable leaf shape, compact growth habit, rapid growth rate, and resistance to diseases common to Aglaonema.

The new cultivar originated from a cross made by the inventors of the cultivar *Aglaonema crispum* 'Dow Hybrid' (not patented) as the male or pollen parent with the cultivar *Aglaonema commutatum* 'Malay Lady' (not patented) as the female or seed parent.

The cultivar 'Jewel of India' was discovered and selected by the inventors in 1989 as a plant within the progeny of the stated cross in a controlled environment in Bangalore, India. Asexual reproduction of the new cultivar by top cuttings, stem cuttings and divisions taken in Bangalore, India, has shown that the unique features of this new Aglaonema are stable and reproduced true to type in successive generations.

The new Aglaonema has not been observed under all possible environmental conditions. The phenotype may vary somewhat with variations in environment such as temperature, light intensity and fertilizer rate, without, however, any variance in genotype.

The following traits have been repeatedly observed and are determined to be the unique characteristics of 'Jewel of India'. These characteristics in combination distinguish 'Jewel of India' as a new and distinct cultivar:

1. Plants of the new Aglaonema grow rapidly, yet plants are compact in growth habit.
2. Plants of the new Aglaonema have an unique and distinct multicolored foliage pattern with prominent and persistent dark green and grayed green spots and blotches on shiny silvery green leaves. The leaf margin is dark green and leaves are narrowly lanceolate and relatively small compared to other commercially-available Aglaonemas.
3. Leaf petioles of the new Aglaonema are speckled with white spots giving a marbled appearance.
4. Plants of the new Aglaonema produce divisions readily giving plants a full and dense appearance.
5. Plants of the new Aglaonema initiate and develop roots rapidly.

6. Plants of the new Aglaonema have good postproduction longevity as plants are very tolerant of low light conditions.
7. Plants of the new Aglaonema are tolerant of low winter temperatures and typically do not exhibit cold injury.
8. Plants of the new Aglaonema are exceptionally resistant to diseases common to Aglaonema.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The first sheet of photographs comprises a side perspective view (top photograph) and a top perspective view (bottom photograph) of a typical single plant of 'Jewel of India'.

The second sheet of photographs comprises a close-up view of the base of a single plant of 'Jewel of India' (top photograph) showing the numerous divisions formed and a close-up view of the upper surfaces of fully-expanded leaves (bottom photograph). Leaf colors in the photographs may appear different from the actual colors due to light reflectance.

DETAILED BOTANICAL DESCRIPTION

The following observations, measurements and comparisons describe plants grown in Zolfo Springs, Fla., under a polypropylene-covered shadehouse and conditions which closely approximate those used in horticultural practice. Plants were grown under day temperatures ranging from 21° to 38° C. and night temperatures ranging from 7° to 21° C. The polypropylene shade provided a 84 percent decrease in ambient light levels.

In the following description, color references are made to The Royal Horticultural Society Colour Chart except where general terms of ordinary dictionary significance are used.

Botanical classification: *Aglaonema hybrida* cultivar 'Jewel of India'.

Parentage:

*Male parent.*—*Aglaonema crispum* 'Dow Hybrid' (not patented).

*Female parent.*—*Aglaonema commutatum* 'Malay Lady' (not patented).

Propagation:

*Method.*—By top cuttings, stem cuttings and by division.

*Time to initiate roots.*—Summer: About 14 days at 27° to 35° C. Winter: About 20 days at 20° to 25° C.

*Time to develop roots.*—Summer: About 21 days at 27° to 35° C. Winter: 30 to 35 days at 20° to 25° C.

*Root description.*—Thick, fibrous, fleshy, and white in color.

Plant description:

*Plant shape.*—Compact and upright, but outward spreading, inverted triangle, symmetrical. Numerous divisions give plants a very full, dense appearance.

*Growth habit.*—Erect when young, becoming more outwardly arching and spreading as leaves develop.

*Plant size.*—Appropriate for 10 to 14-cm containers. Height, soil surface to top of leaf canopy: About 27 cm. Width: About 45 cm.

*Plant vigor and growth rate.*—Vigorous, rapid growth rate. Plants will form about 15 divisions within 31 weeks of planting a rooted top cutting.

*Foliage description.*—Leaf shape: Young: Narrowly lanceolate. Fully-expanded: Narrowly lanceolate. Leaf length, fully expanded: About 19 cm. Leaf width, fully expanded: About 5 cm. Margin: Entire. Leaf surface: Flat, undulating. Leaf tip: Acuminate. Leaf base: Obtuse to cordate. Leaf aspect: Erect initially, eventually mature leaves held horizontal to the stem. Leaf texture: Leathery, thick, smooth, glabrous. Leaf color: Young, upper surface: Background: Silvery green, close to 147B, shiny. Random spots and margin: Dark green, 147A. Random spots: Grayed green, 189A. Young, lower surface: Greener and slightly lighter than 147B with darker green areas, dull. Mature, upper surface: Background: Silvery green, close to 147B, shiny. Random spots and margin: Dark green, 147A. Random spots: Grayed green, 189A. Mature, lower surface: Greener and slightly lighter than 147B with darker green areas, dull. Petiole length, primary shoot: About 11 cm. Petiole diameter, primary shoot, at leaf base: About 4 mm. Petiole diameter, primary shoot, at stem: About 7 mm Petiole wing: Length: About 8.5 cm. Width: About 6 mm. Petiole color: Young: 146A. Mature: 146A/147A with random white spots, marbled. Venation: Upper surface, midvein: 147A. Lower surface, midvein: 147B.

*Inflorescence.*—Typical of Aglaonema, no commercial significance.

Disease tolerance: Plants of the new Aglaonema are exceptionally resistant to diseases common to Aglaonema.

It is claimed:

1. A new and distinct cultivar of Aglaonema plant named 'Jewel of India', as illustrated and described.

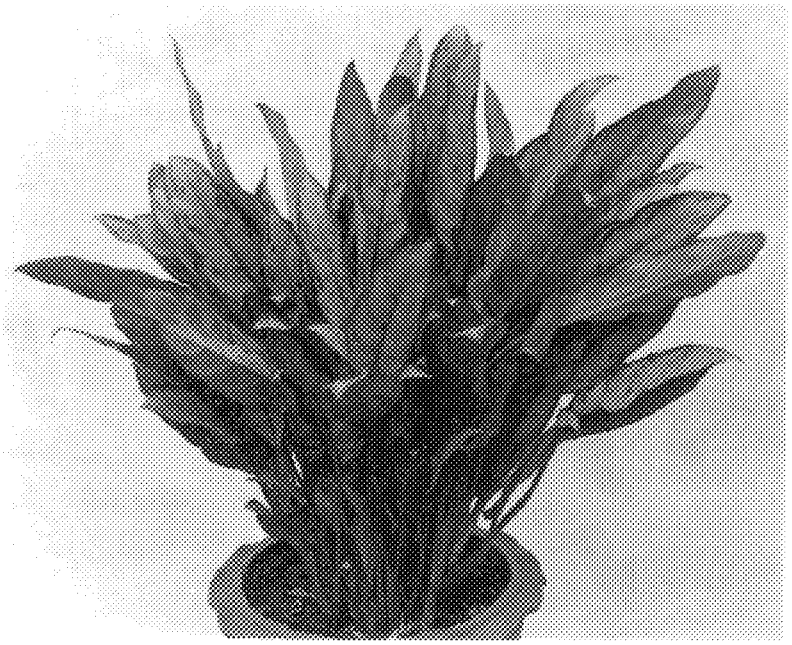
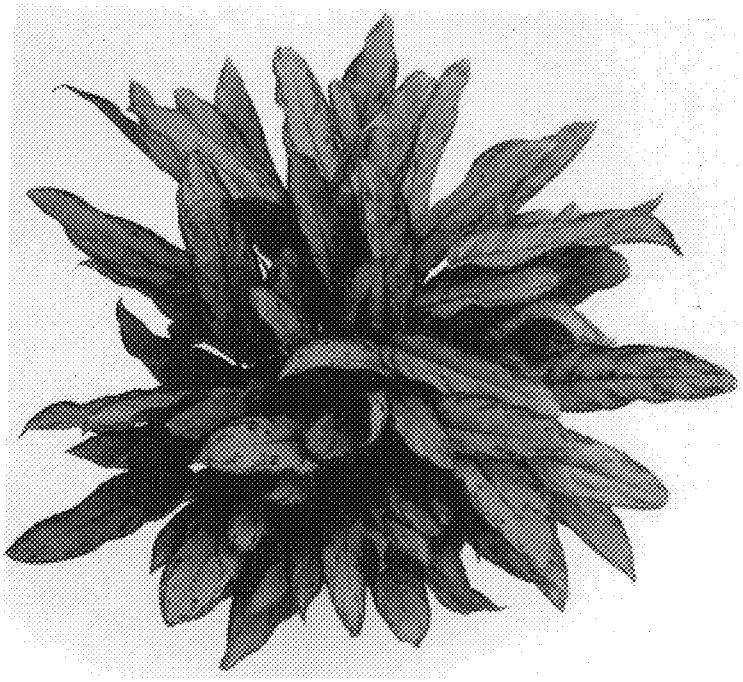

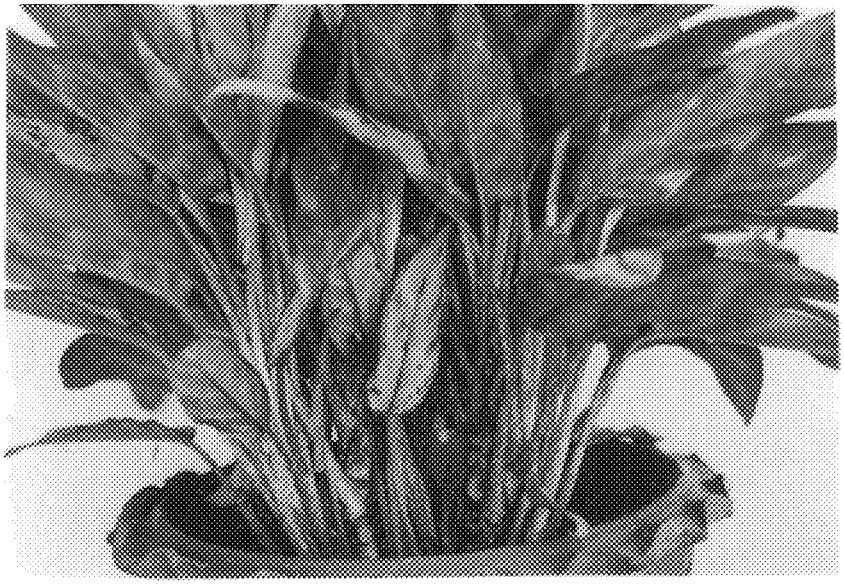
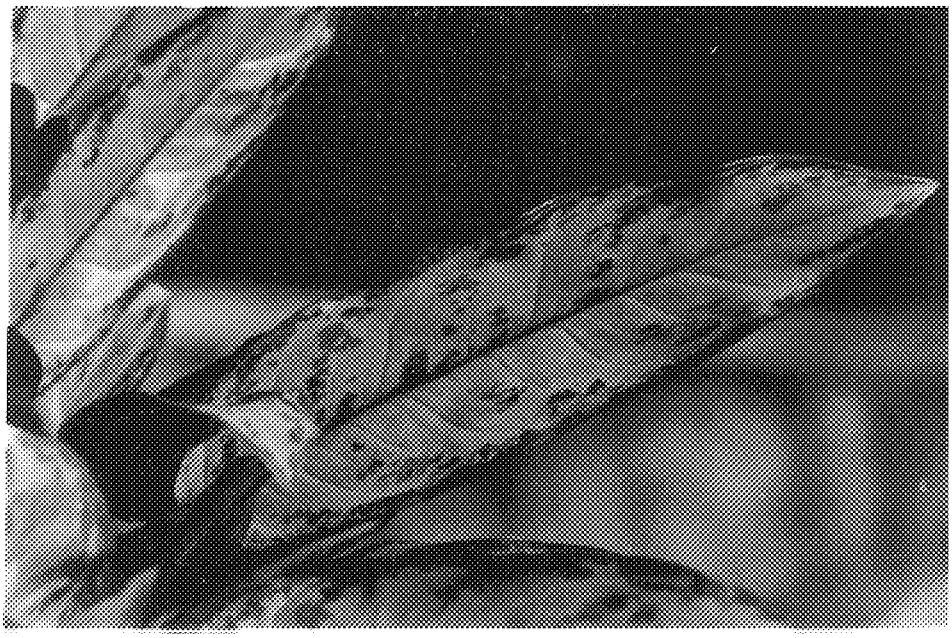

* * * * *